United States Patent
Suckau et al.

(10) Patent No.: US 7,873,478 B2
(45) Date of Patent: Jan. 18, 2011

(54) MASS SPECTROMETRIC DIFFERENTIATION OF TISSUE STATES

(75) Inventors: Detlev Suckau, Grasberg (DE); Martin Schürenberg, Tarmstedt (DE); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 859 days.

(21) Appl. No.: 11/195,365

(22) Filed: Aug. 2, 2005

(65) Prior Publication Data

US 2006/0063145 A1 Mar. 23, 2006

(30) Foreign Application Priority Data

Aug. 3, 2004 (DE) ........................ 10 2004 037 512

(51) Int. Cl.
*G06F 19/00* (2006.01)
*G01N 24/00* (2006.01)
*H01J 49/00* (2006.01)

(52) U.S. Cl. .................... 702/19; 436/173; 250/281; 250/287

(58) Field of Classification Search .................... None
See application file for complete search history.

(56) References Cited

U.S. PATENT DOCUMENTS

| | | | |
|---|---|---|---|
| 5,770,272 A | 6/1998 | Biemann et al. | |
| 5,808,300 A | 9/1998 | Caprioli | |
| 6,531,318 B1 | 3/2003 | Palmer-Toy et al. | |
| 6,756,586 B2 | 6/2004 | Caprioli | |
| 6,824,981 B2 * | 11/2004 | Chait et al. .................... | 435/6 |
| 2003/0073145 A1 | 4/2003 | Caprioli | |
| 2006/0160077 A1 * | 7/2006 | Lausmaa et al. ................ | 435/6 |

FOREIGN PATENT DOCUMENTS

WO WO 03/034024 A3 4/2003
WO WO 03/104794 A1 12/2003

OTHER PUBLICATIONS

Stoeckli et al. (Nature Medicine (2001) vol. 7, No. 4, pp. 493-496).*
Luxembourg, et al., "Effect of Local Matrix Crystal Variations in Matrix—Assisted Ionization Techniques for Mass Spectrometry", Anal. Chem., vol. 75, pp. 2333-2341, American Chemical Society, 2003.
Stoeckli, et al., "Molecular imaging of amyloid β peptides in mouse brain sections using mass spectrometry", Analytical Biochemistry, vol. 311, pp. 33-39, Elsevier Science, 2002.
Pusch, et al., "Mass spectrometry-based clinical proteomics", Pharmacongenomics, vol. 4, pp. 463-476, Ashley Publications Ltd., 2003.
Stoeckli, et al., "Molecular Imaging of Amyloid β Peptides in Mouse Brain Sections Using Mass Spectrometry", Analytical Biochemistry 311, 2002, pp. 33-39, Academic Press.

* cited by examiner

*Primary Examiner*—Lori A Clow
(74) *Attorney, Agent, or Firm*—Law Offices of Paul E. Kudirka

(57) ABSTRACT

The invention relates to the determination and visualization of the spatial distribution of tissue states in histologic tissue sections on the basis of mass spectrometric signals acquired so as to be spatially resolved. The invention provides a method which determines the tissue state for the tissue spots as a state characteristic, which is calculated as a mathematical or logical expression from at least two mass signals of this tissue spot, and which indicates the tissue state as a gray-level or false-color image in one or two dimensions.

12 Claims, 1 Drawing Sheet

MASS SPECTROMETRIC DIFFERENTIATION OF TISSUE STATES

FIELD OF THE INVENTION

The invention relates to the determination and visualization of the spatial distribution of tissue states in histologic tissue sections on the basis of spatially resolved mass spectrometric signals.

BACKGROUND OF THE INVENTION

The term "tissue state" here means the state of a small subarea of a tissue section with respect to a stress, a pathological change, an infection or other type of change compared with a normal state of this tissue. The tissue state must therefore be identifiable as a concentration pattern of substances which can be detected in this small subarea by a mass spectrometer. The substances can be peptides or proteins which are under- or overexpressed and hence form a pattern, or they can include positranslational modifications of proteins, their breakdown products (metabolites), or collections of other substances in the tissue.

Mass spectrometry with ionization of the samples by matrix-assisted laser desorption and ionization (MALDI) has been used successfully for several years for the determination of molecular weights, and for the identification and structural characterization of proteins. In this case, the protein is usually dissolved and mixed with a solution of a matrix substance such as sinapic acid before being applied to the sample support. The solvent then evaporates and the matrix substance crystallizes, the protein crystallizing with it in the matrix crystals. Bombarding the sample obtained in this way with sufficiently energetic short pulses of laser light leads to the matrix substance absorbing energy and evaporating explosively as a result. The proteins are entrained into the gaseous cloud inside the mass spectrometer and ionized by protonation. The ions are then separated in the mass spectrometer according to their mass-to-charge ratios (m/z) and measured as a mass spectrum. Their mass can be determined from the mass spectrum. Since ionization by matrix-assisted laser desorption essentially provides only singly charged ions, in the following, we will simply refer to "mass determination" and not determination of the mass-to-charge ratios and, correspondingly, just the "mass" of the ions instead of their m/z-ratio.

These analyses can be carried out on biological samples, such as tissue homogenates, lyzed bacteria or biological fluids (urine, blood serum, lymph, spinal fluid, tears, sputum), the samples generally being subjected to sufficient fractionation beforehand by chromatographic or electrophoretic techniques.

For this purpose it is advisable to free the samples from interfering impurities, such as certain buffers, salts or detergents, which reduce the efficiency of the MALDI analyses. The analysis of biological samples usually involves very time-consuming sample preparation, particularly if, at the same time, information concerning the distribution of a protein in different regions of a tissue is to be obtained. "Laser capture microdissection", for example, can achieve this, but the time-consuming processing described above is still necessary; there is also the difficulty of obtaining sufficient material for this type of analysis.

Imaging mass spectrometry (IMS) makes it unnecessary to go to these lengths. With this method, a microscopic tissue section is produced from a piece of tissue taken from a human or animal organ of interest using a microtome, for example, and laid on a specimen slide. A matrix capable of absorbing laser energy is then applied to the surface of the specimen, for example by pneumatic spraying onto a moving support (U.S. Pat. No. 5,770,272; Biemann et al.). There are two different methods for the subsequent mass spectrometric scan: The raster scan method and stigmatic imaging of the ions of a small region.

The raster scan method produces a one- or two-dimensional intensity profile for individual proteins by scanning a microscopic tissue section with well-focused laser beam pulses in a MALDI mass spectrometer, the proteins being identifiable in the mass spectra (U.S. Pat. No. 5,808,300; Caprioli). Each spot is therefore irradiated at least once with a finely focused pulse of laser light and provides a mass spectrum which can cover a broad range of molecular weights, for example 1 to 30 kilodaltons. Using suitable software, it is then possible to define an ion mass, which represents a peptide or a protein, or a narrow mass range around this mass, in the spectra and to graphically represent its intensity distribution over the surface of the microscopic tissue section. Using this method, it has been possible to correlate the distribution of neuropeptides in the brain of a rat with specific morphological features, for example, or to depict the distribution of amyloid beta peptides in the brains of Alzheimer animal models. It is possible to visualize sections of the brain affected by "Alzheimer plagues" with precise spatial definition (Stoeckli M, Staab D, Staufenbiel M, Wiederhold K H, Signor L, Anal Biochem. 2002, 311, 33-39: Molecular imaging of amyloid beta peptides in mouse brain sections using mass spectrometry).

The method of stigmatic imaging irradiates a defined area of up to 200 by 200 micrometers with the laser pulse. The ions formed over the area are imaged ion-optically, spot by spot on a spatially-resolving detector. So far, it has been possible to scan distribution images of these ion masses by selecting individual ion masses with this method (S. L. Luxembourg et al., Anal. Chem. 2003; 75, 1333-41); it is to be expected, however, that very fast cameras will be able to scan complete mass spectra for every spot of the area.

A considerable disadvantage of both methods is the fact that, until now, only individual features in these types of spectra have been utilized analytically, for example a peptide present in a high concentration, which is particularly typical of certain tissue states within a tissue sample. This procedure has limited the method until now and prevented a broader application for those tissue states which cannot be attributed to the appearance of one single peptide or protein.

Independently of such imaging methods, targeted searching for "markers" has developed as an interesting field of clinically oriented research (W. Pusch et al., Pharmacogenetics 2003; 4, 463-476). Here, bodily fluids such as blood, urine or spinal fluid, but also tissue extracts, are typically processed into coarse fractions with a less complex analyte composition by extracting them with- chromatographic phases, solid phase extraction or other selective methods before they are mass spectrometrically characterized. The mass spectra obtained by this method display a more or less complex pattern which originates from peptides and proteins. By comparing the mass spectra of samples from healthy and sick individuals it is possible, in individual cases, to find single peptides or proteins which are characteristic of the medical condition of the individuals.

However, there is a general opinion that interesting distinguishing features with better statistical evidence can only be discovered when this method is performed on dozens or hundreds of samples from two so-called cohorts of individuals— one cohort serving as a reference and one cohort in which certain peculiarities or deviations in the spectra are expected because a specific clinical picture, such as intestinal cancer or prostate cancer, is present.

This approach has achieved preliminary successes with the discovery of distinct and statistically significant protein signals in the case of samples from ill persons. In the literature, however, a vehement argument is in progress about whether these markers can be used for diagnosis or not since, as yet, it has not been possible to establish whether these markers might simply be indicative of the patient's type of medication or a general stress situation associated with the illness. For the licensing of such markers for general diagnostic purposes, the United States FDA (Food and Drug Administration) now requires, as a minimum, that the protein found as a marker is unambiguously identified and that knowledge of the protein and its function (or its breakdown pathway, if the substance in question is a breakdown product) is used to at least establish the plausibility of a link with the illness concerned.

The objective of these analyses is naturally to make an early prediction about the possible development or proliferation of various diseases in the future of an individual. It is hoped that it will be possible to identify cancer at a very early stage, for example, and therefore to have a much better chance of fighting it.

In general, however, the mass spectra of the various cohorts do not contain any simple features such as a few individual signals whose intensities differ significantly in the cohorts. Complex mathematical-statistical analyses of the mass spectra of the various cohorts must therefore usually be carried out. These analyses can be carried out using a plurality of methods, which analyze whether it is possible to distinguish between the cohorts of healthy patients and sick patients unambiguously and to a statistically significant degree on the basis of groups of features in the mass spectra.

It is, for example, possible for a principal component analysis (PCA) to determine whether cohorts of sick individuals (or, where possible, even several cohorts with several related diseases) can be distinguished from each other and from cohorts of healthy reference individuals. If this is the case, a further mathematical computational method can use the mass spectrometric signals to calculate disease-specific distinguishing characteristics which make it possible to unambiguously identify the state of an individual with respect to a specific disease. Suitable mathematical transformations can, for example, make it possible for the disease-specific distinguishing characteristics to cover the range from minus infinity to plus infinity, for example, where all values less than zero correspond to a healthy state and all values greater than zero to a diseased one. A very simple distinguishing characteristic can be a simple concentration ratio of two proteins, for example, where the range extends from zero to infinity. Alternatively, the distinguishing characteristics are transformed in such a way that they cover the range from zero to one: healthy state close to zero, diseased state close to one. The detailed computational method for calculating the distinguishing characteristics (both the algorithm and the parameter values) is saved and later used for the diagnosis of this disease using mass spectra scanned from this individual's samples.

Genetic algorithms (GA) generate a decision path along which the medical condition of an individual can be determined. A logical expression can be obtained from the decision path which, in turn, can be transformed into a characteristic which distinguishes between different states. This logical computational method is also saved and later used for diagnosis of other samples.

Other methods for analyzing the differentiation have been elucidated, including: linear discriminance analysis (LDA), support vector machines (SVM), neuronal networks (NN), learning vector quantification (LVQ).

From the results of such statistical analyses, it is ultimately possible to obtain detailed computational methods (algorithms plus parameter sets) to calculate distinguishing characteristics that are represented as mathematical or logical expressions, each incorporating several spectra signals. These can also include very weak spectral signals. The distinguishing characteristics also seem to make it possible to represent more subtle differences between samples from different cohorts. However, the number of samples required easily runs into thousands.

It is a considerable problem here that the variation in the ion signals in the individual mass spectra, even within one cohort (patient or healthy), is large, and, for example, the age distribution in a group or the gender-specific distribution can have much more influence than the effect which is to be investigated. One of the reasons for this is the fact that the analysis of bodily fluids only provides a remote—or indirect—picture of the occurrence of the disease at the site of action (for example the tumor or the brain in the case of neuro-degenerative diseases). According to present expectations, the problem of the search for markers could be simplified if it were possible to compare healthy and diseased samples from a single individual. But this is not possible when the samples are bodily fluids because of their homogenization in the body, and can, at best, be determined as a temporal variation over relatively long periods of time.

SUMMARY OF THE INVENTION

The invention provides a method which, on the one hand, can provide a visual representation of the mass spectrometric differentiation of tissue states and, on the other, can formulate characteristics which distinguish between healthy and diseased tissue sections using spatially resolved mass spectrometric signals of the analyzed tissue, and can do this more easily than is the case with samples analyzed on a cohort basis.

The invention first provides a method which is suitable for visualizing the spatial distribution of tissue states of histologic samples. It comprises the following steps:
a) production of at least one histologic sample as a tissue section,
b) preparation of the samples for mass spectrometric analyses,
c) spatially distributed detection of mass spectrometric signals along one or two dimensions of the samples,
d) calculation of localized characteristics which distinguish between different states from at least two mass spectrometric signals, and
e) graphic representation of the spatial distribution of these distinguishing characteristics for at least one of the samples.

It is advisable to carry out the calculation on a computer and the tissue imaging on a screen. This makes it possible to lay a microscopic image of the tissue section (or tissue sections) true to position under the image of the distinguishing characteristics. For this, the microscopic image is represented as a color density image (brightness), for example, and the distinguishing characteristics as shades of false color (example: blue tissue is healthy; red is diseased).

For this purpose, the calculation of the localized distinguishing characteristics can utilize detailed computational methods (algorithms and parameter sets) which have been previously obtained from cohorts of healthy and diseased tissue homogenates.

However, since, as shown above, these computational methods are based on widely varying samples from different individuals and can therefore impair clear detectability, a further embodiment of the invention will focus on the differences between healthy and diseased tissue of the same individual. It can be expected that the direct analysis of a tumor tissue and the surrounding healthy tissue in the sample from an individual could reveal differences of far greater specificity between healthy and diseased tissue. Thus, in the image of one or more pieces of tissue on the screen, regions can be indicated which are considered as healthy or diseased. From the mass spectra of these regions it is possible to independently develop (on the computer, by means of predetermined development procedures) computational methods for the characteristics which distinguish between different states. These can then be applied to all spots of the tissue. The distinguishing characteristics are then displayed in the image of the tissue. The computational method can follow a previously determined algorithm, for example, where only the parameter set is optimized. So-called "supervised learning" is one such possibility.

Furthermore, the spatially resolved mass spectra can also be scanned from a copy of the sample, i.e. not from the tissue itself. The peptides or proteins of a tissue section can be transferred onto a blot membrane, for example. Alternatively, they can be transferred onto a surface which is coated with one or more types of antibodies. It is thus also possible to display the spatial distribution of peptides or proteins at very low concentrations. The tissue state characteristics can thus be extended to ratio differences of posttranslational modifications such as phosphorylations or glycosylations, or to breakdown forms of proteins.

BRIEF DESCRIPTION OF THE DRAWINGS

The above and further advantages of the invention may be better understood by referring to the following description in conjunction with the accompanying drawings in which.

DETAILED DESCRIPTION

Figure 1A:
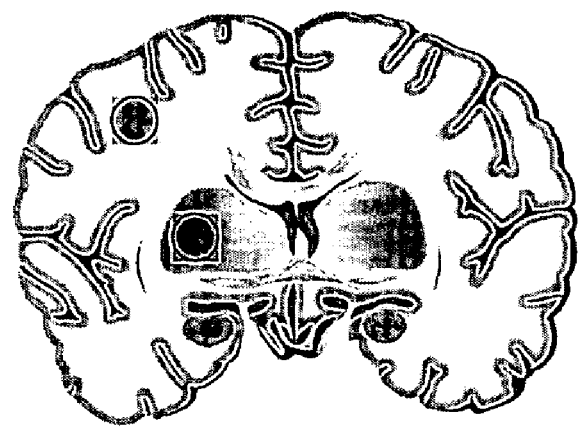
FIG. 1A shows a schematic microscopic section of a mouse brain in which two circular areas are defined whose mass spectra, scanned on a spot-by-spot basis, are used to develop the calculation method for the characteristics which distinguish between different states.

One preferred embodiment begins with the production of a microscopic tissue section, preferably from a deep-frozen piece of tissue, with a microtome. The microscopic tissue section is applied to a suitable support. This support can be a glass specimen slide, for example, whose surface is equipped with a transparent but conductive surface coating for subsequent use in the mass spectrometer. Other supports, for example metal supports or supports made of electrically conductive plastic, can also be used, however. The microscopic tissue section can then be stained in the usual way, although care has to be taken to use a stain which does not interfere with a subsequent mass spectrometric analysis of the tissue constituents. Fluorescence dyeing methods can also be used if they do not restrict the mass spectrometric analysis.

After this, a microscopic image is taken, with transmitted or reflected light, from the microscopic tissue section, and is later used to lay under the result images. Before the image is taken, markings which are recognizable both optically as well as mass spectrometrically can preferably be applied to the support to facilitate subsequent adjustment so as to obtain a true position. Many mass spectrometers are equipped with a viewing unit for the samples, which can likewise be used for the true-to-position adjustment.

The microscopic tissue section is then sprayed with a solution of a suitable matrix substance for ionization by matrix-assisted laser desorption. The spraying can be done on a device which moves the specimen slide under the spray jet so that a uniform sprayed layer is achieved, for example. Care must be taken to ensure that the positional accuracy of the samples is not adversely affected by the sprayed liquid running. During this process, the matrix substance which is crystallizing out absorbs such substances from the microscopic section as can be integrated into the microcrystals themselves or into grain boundaries between the microcrystals during the crystallization.

The choice of matrix substance can greatly influence which biomolecules in the spectra lead to signals. Proteins are prepared for MALDI MS analysis with 2.5 dihydroxybenzoic acid (DHB) or sinapic acid (SA), for example; peptides with α-cyano-4-hydroxycinnamic acid (CCA), nucleic acids with 3-hydroxypicolinic acid (3-HPA) and saccharide-carrying structures with DHB or trihydroxyacetophenone.

In another similarly favorable embodiment, spatially resolved mass spectrometry can be carried out on a copy rather than on the original tissue section. It is thus possible, for example, to bring the moist microscopic tissue section into contact with a blot membrane either before or after the microscopic image is taken. Blot membranes are known from two-dimensional gel electrophoresis; they can bind proteins and peptides by their affinity in a particular way so that they are stationary. The substances can be transferred onto the blot membrane by simple diffusion and also by electrophoresis. Dinitrocellulose membranes are particularly favorable for use as blot membranes for mass spectrometric analyses. These blot membranes are then used instead of the microscopic tissue sections for the mass spectrometric analysis.

A surface which is densely coated with an antibody can be used as the copy medium in place of a blot membrane. This makes it possible to extract various mutants, modification forms and also breakdown forms of a single protein from the tissue and to analyze them with spatial resolution, even if the protein is only present in the tissue at a very low concentration. According to the invention, the ratios of the mutants, modification forms and the breakdown forms can be visualized as tissue state characteristics. It is interesting and extremely informative, for example, to see how a protein occurs mainly in singly phosphorylized form at some sites in the tissue, while at other sites it is triply phosphorylized.

The surface of the copy medium can also be coated with more than one antibody, however, so that several proteins can be fished simultaneously. If the fishing does not take place up to saturation, the ratios of the proteins can again be represented as characteristics which distinguish between different tissue states.

The samples, either the prepared microscopic tissue sections or the prepared copies, are then introduced into the mass spectrometer. The mass spectrometric scans are then carried out using either the raster scan method with a finely focused pulsed beam of laser light or the scanning method with stigmatic imaging of the ions generated over a large area.

The raster scan consists of a spot-by-spot acquisition of the mass spectra, the finely-focused laser beam carrying out one acquisition, or preferably many acquisitions, of mass spectra at each spot of the tissue sample (or blot membrane sample). The mass spectra of the same spot are added together in order to achieve a higher dynamic range of measurement and also to improve the statistics of the mass signals. The diameters of the "spots" correspond roughly to the diameter of the laser focus, or to be more precise, the diameter of the laser beam on the sample, which can be adjusted by focusing. For the purposes of the raster it is usually possible to set diameters of around 10 to 50 micrometers. YAG lasers also permit focus diameters of less than one micrometer, but no applications are known. The sum spectra are stored for every spot of the raster. For a tissue area of one square millimeter there can thus be 400 to 10,000 mass spectra, the normal figure being around 1,000 to 2,000.

The raster is generally made up of measuring spots arranged in a square, a parallelogram or a honeycomb shape, but it can, of course, dispense with this type of pattern and following a specific morphology of the sample, as would be helpful, for example, in the case of an axon of a ganglion several millimeters long. The only important thing is that the separations of the measuring spots are adjusted to match the size of the area irradiated by the laser.

Ions generated from spots by MALDI can be analyzed with different types of mass spectrometers. Time-of-flight mass spectrometers (TOF-MS), with or without ion reflectors, are the usual method. Time-of-flight mass spectrometers with orthogonal ion injection can also be used. Ion traps and Fourier transform ion cyclotron resonance (FT-ICR) are also being used increasingly.

The stigmatic image generates around 100 to 2,000 spatially resolved mass signals from an irradiated surface of around 100 to 200 micrometers in diameter on a spatially-resolving detector. Time-of-flight mass spectrometers with special ion focusing systems for stigmatic imaging are used for this. The current art consists in acquiring only the ion current signal for each laser pulse over a narrow mass range, and masking out the remaining mass ranges, since the time resolution of the detectors permits no other way of measuring. For each of the other mass ranges the measurements must be repeated. The mass ranges are chosen according to those masses which have proven to be significant in previous analyses. It is, however, to be expected that, in future, there will be cameras with better time resolution. It will then be possible to scan the complete mass spectra for a multitude of spots, although the question of the mass resolution power is as yet unanswered. The spatial resolution of this method promises to be better than that of the raster scan. Relatively large areas are scanned one after the other like a mosaic.

After the measurements, complete or partial mass spectra are then available for each tissue spot. From these data it is possible to calculate the characteristics which distinguish between different tissue states for each spot, which is calculated as a mathematical or logical expression from at least two mass signals (usually more) of this tissue spot. This involves the use of the detailed computational methods comprising algorithms and parameter sets obtained in preliminary analyses of cohorts of samples. These tissue state characteristics are then represented graphically—preferably over the microscopic image.

A preferred representation of this tissue image consists in using the microscopic image showing the structure of the tissue for the color density (brightness of the image), and using the tissue state characteristic for the color shade. It is then possible to visualize healthy parts of the tissue in blue, diseased parts in red, and the tissue structures in light-dark shades of the respective color, for example. This type of representation produces a higher resolution of the tissue state characteristics for the eye than is provided by the measurements.

Figure 1B:
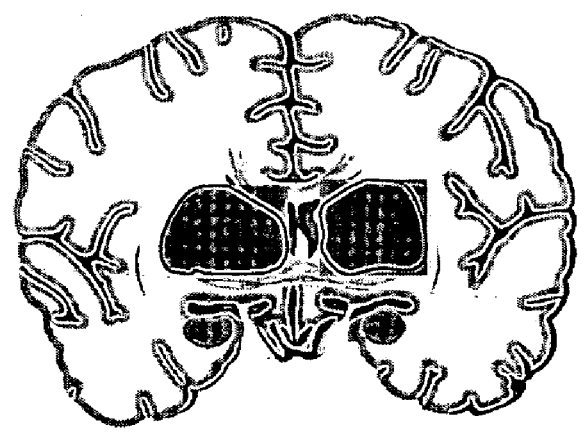
FIG. 1B shows a section like that of FIG. 1A with a characteristic distribution over the whole tissue section.

In a further embodiment of the invention, the computational methods for the tissue state characteristics can also be developed, or at least refined, using the mass spectra of the tissue itself (or of two different pieces of tissue). In the tissue image on the screen it is then also possible to indicate regions which are considered to be healthy or diseased (FIG. 1A). From the mass spectra of these regions it is then possible to develop computational methods for distinguishing characteristics, independently on the computer using predetermined guidelines. The computational method can follow a previously determined algorithm, for example, where the parameter set is merely optimized. A plurality of learning methods have been elucidated for this type of optimization. It is also possible to develop a new computational method according to a given development scheme, independently on the computer. The improved or newly-developed computational method is then applied to all spots of the tissue, the calculated distinguishing characteristics being represented in the tissue image (FIG. 1B).

It can also be interesting to compare more than two groups of spectra with each other. In this case, several group-defining areas are marked in the tissue section, or spread over several tissue sections, and the characteristics are determined in such a way that the groups can be distinguished from each other.

A further embodiment avoids the acquisition of spectra which are not to be used analytically if the regions to be compared are clearly recognizable. In the case of a spatially limited tumor, for example, it can thus be sufficient to mark this and a representative small part of the healthy tissue in the image of the tissue section. Only these two areas, which are to be used for determining the characteristics, are then actually measured.

In further embodiments, three-dimensional images of a tissue, through several layers of microscopic tissue sections, for example, can also be scanned and visualized according to the invention.

The invention claimed is:

1. A method for the detection and visualization of the spatial distribution of tissue states of a tissue section comprising:
   a) preparing the tissue section for a mass spectrometric analysis on a support;
   b) at each of a plurality of localized spots physically spaced apart along one or two dimensions of the tissue section, performing a measurement with a mass spectrometer that produces a primary ion mass spectrum with a plurality of mass signals for that spot;
   c) at each of the plurality of spots, combining at least two different mass signals of the plurality of mass signals produced at that spot, the two different mass signals representing two different substances, with predetermined mathematical or logical expressions to generate a combination value that represents a tissue characteristic at that spot; and
   d) displaying the combination values generated in step (c) at the corresponding physical spot positions to provide a visualization of the spatial distribution of tissue states of the tissue section.

2. The method according to claim 1, wherein step (d) comprises displaying the combination values with brightness levels or false colors.

3. The method according to claim 1 further comprising superimposing a microscopic image of the tissue section true to position under the display of the spatial distribution of the tissue states.

4. The method according to claim 3, wherein the microscopic image of the tissue section is represented by different color densities and the spatial distribution of the tissue states is represented by shades of color.

5. The method according to claim 1, wherein the mathematical or logical expressions used in step (c) are obtained from previous mathematical analyses of large numbers of sample measurements.

6. The method according to claim 1, wherein the mathematical or logical expressions used in step (c) are obtained from mathematical analyses of the mass spectrometric signals of two defined regions of the tissue section.

7. The method according to claim 6, wherein the two regions for the mathematical analyses of mass spectrometric signals are defined by reproducing the image of the tissue section on a computer screen.

8. The method according to claim 1 further comprising preparing the tissue sample for the mass spectrometric analyses by transferring substances from the tissue section onto a copy medium, and performing step (b) on the surface of the copy medium.

9. The method according to claim 8, wherein the copy medium is a blot membrane.

10. The method according to claim 8, wherein the copy medium is a surface coated with antibodies.

11. The method according to claim 1, wherein step (b) comprises ionizing portions of the tissue section by matrix-assisted laser desorption.

12. The method according to claim 1, wherein steps (a)-(c) are performed on each of several microscopic tissue areas which are all part of a single tissue sample and, in step (d), the tissue states are represented three-dimensionally.

* * * * *